Figure 1:
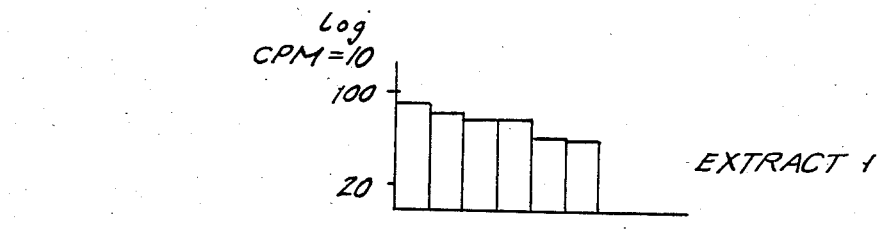
Figure 1:
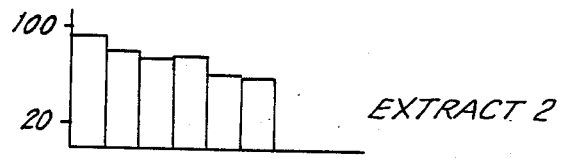

United States Patent [19]

Stevens et al.

[11] Patent Number: 4,605,557

[45] Date of Patent: * Aug. 12, 1986

[54] METHOD OF PRODUCING ALLERGENIC EXTRACTS

[75] Inventors: Erik Stevens, Linden-Lubbeek; Ernestina M. Van Hoeyveld, Lubbeek, both of Belgium

[73] Assignee: Tetra Consultants, Inc., New Rochelle, N.Y.

[*] Notice: The portion of the term of this patent subsequent to Jul. 15, 2003 has been disclaimed.

[21] Appl. No.: 415,567

[22] Filed: Sep. 7, 1982

[51] Int. Cl.⁴ .................. A61K 39/36; A61K 39/00
[52] U.S. Cl. ........................... 424/91; 424/88; 514/2; 514/561
[58] Field of Search .............. 252/403, 177; 424/88, 424/91, 89, 92, 305, 311, 319, 320

[56] References Cited

U.S. PATENT DOCUMENTS 4,226,853 10/1980 Marsh ................................. 424/88
4,258,029 3/1981 Maloney et al. ................... 424/88
4,363,818 12/1982 Gottlieb ............................. 424/319

FOREIGN PATENT DOCUMENTS 1250966 9/1967 Fed. Rep. of Germany ........ 424/85
1808948 7/1969 Fed. Rep. of Germany ...... 514/564
47-1479 1/1972 Japan .................................. 514/561

Primary Examiner—David M. Naff
Assistant Examiner—Shawn P. Foley

[57] ABSTRACT

A method for the production of allergenic extracts comprising the extraction of an allergenic substance with a suitable solvent having incorporated therein a small but effective amount of a compound of the formula,

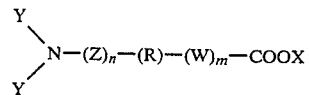

wherein Y is H or lower alkyl; Z is $CH_2$; n is 0 or 1; R is alkylene or cycloalkylene; m is 0 or 1; W is $CH_2$; and X is H, acyl or lower alkyl. The novel allergenic extracts produced by this process are also the subject of this invention.

8 Claims, 4 Drawing Figures

TABLE 1

TABLE 2

● EXTRACT 1
□ EXTRACT 3

TABLE 3

TABLE 4

METHOD OF PRODUCING ALLERGENIC EXTRACTS

The etiology and root causes of the multitude of individual diseases or conditions included within the generic definition of allergy are not completely elucidated or known at this time. The generic condition known in medicine as "allergy" connotes an altered reaction of tissues or other systemic parameters in certain persons on exposure to certain agents which, in similar amounts are innocuous to other persons. These altered reactions of the allergic person may be of various types, ranging from a more or less intense skin sensitivity to a severe and sometimes fatal systemic shock reaction.

At the present time it is the consensus of the medical world that the allergic reactions suffered by all susceptible persons are mediated, if not basically caused by various exciting agents, commonly referred to as "allergens" or "antigens". The presence of these allergens cause, in those individuals who are sensitive to the specific allergens involved, the production of specific antibodies or sensitized cells. The interaction of antibodies with allergens by some mechanism not fully appreciated, cause allergic symptoms. Common manifestations of the type of allergic symptoms usually seen in persons suffering a so-called immediate-type "allergic attack" are such conditions as "hay fever" i.e., runny nose and watery eyes, asthmatic reactions, gastrointestinal disturbances, urticaria edema and shock.

A person who is allergic may be sensitive to only one allergen, but multiple sensitivities are the rule. The various types of allergens to which a patient may be susceptible are found in such allergic materials as inhalants, for example, pollens, fungi, vegetable or animal epithelia, cosmetics, and house dust components; foods, for example, eggs, shellfish, and strawberries; infectious agents, for example, bacteria, fungi, molds, parasites, such as, mites, ticks or fleas; and contactants, for example, plants, flowers, chemicals, furs, and cosmetics. These allergic materials may contain one or more allergens to which the patient is sensitive and exposure to these allergic materials will, in the susceptible individual, cause an allergic attack, manifested by one or more allergic symptoms, the severity of which depends upon the degree of exposure as well as the nature of the allergic material to which the patient is exposed.

It is important to determine the types of allergic materials and/or allergens to which the allergic person is susceptible. This determination is required in order to know which allergic materials the patient is to be isolated from as well as to ascertain the type of treatment which will be required to prevent, ameliorate or therapeutically treat the patient. The diagnostic procedures that have been developed to date include one that is most commonly employed to determine the identity of the allergens to which the patient is sensitive, the skin test. In the skin test diagnostic procedure a small amount of an extract of the allergen is administered cutaneously to the patient and the local allergic reaction, i.e., wheal and flare, observed to determine the patients sensitivity to the test allergen.

Once the identity of the allergens to which the patient is sensitive has been determined, the type of therapeutic treatment required to prevent future allergic attacks can be decided upon. Where the total elimination of the allergen from the presence of the patient is not feasible, for example, where the allergen is a pollen or house dust component, one of the prime methods of treatment is that of desensitization or hyposensitization. This method of treatment involves the successive injecting of an extract of the causitive allergen in a series of gradually increasing doses until the patient slowly builds up an immunity threshold which will permit exposure to a normal concentration of the allergen without the initiation of an allergic attack.

The extracts of the allergens which may be employed in both the diagnostic and desensitization procedures are well known and are usually produced by the following procedures. An allergic material is extracted by treatment with a solvent in which the allergen is soluble. Usually the allergic material, such as pollen, house dust, molds, mites, animal dander, or various foods, are extracted with an aqueous solvent for example, distilled water. However, other extraction solvents have also been successfully employed in the production of the desired allergen extract, for example, pyridine/aqueous alkaline extraction solutions, as well as various alcoholic solutions, such as, ethanolic solutions, have been used. The solvent extraction of the allergic material yields a solvent extract containing the allergens from the allergic material which are soluble in the selected solvent. This allergen-containing solvent extract may then be concentrated to provide a composition possessing a high concentration of allergens. Alternatively, the allergen containing solvent extracts can be dried, for example, by lyophilization, to be stored for future systemic administration upon reconstitution with a suitable systemically administerable vehicle, for example, pyrogen-free water for injection.

It is well recognized that, as presently practiced, both diagnostic and desensitization procedures suffer from serious disadvantages. The allergen extracts presently employed in the practice of these procedures have the ability to degrade and lose substantial potency within a short time after their production or reconstitution, if they are stored in the dried state for later use. In addition, it is well known that desensitization procedures must be carried out with great caution, especially in those cases where the allergen is highly potent or the patient is extremely sensitive. Severe reactions may result from overdosage of the allergen extract, or too rapid an increase in the dosage thereof, or by accidental introduction of the extract into a blood vessel, such as a vein. The reactions involved may range from severe local reaction and swelling at the site of injection to severe systemic reaction, including anaphylactic shock and death.

We have now discovered a process of producing the allergen containing extracts adapted for systemic administration to patients and which are suitable for use in the diagnosis and which are suitable for use in the diagnosis and therapeutic treatment of allergic conditions while avoiding the disadvantages of the prior art. More particularly, we have discovered that the disadvantages presently encountered in connection with the use of allergen-containing extracts are obviated if the allergen extracts are produced in accordance with the procedures of this invention. Even more particularly, we have found that an allergen containing extract composition may be produced by extracting an allergic material with a suitable solvent which has incorporated therein a small but effective amount of a compound of the formula,

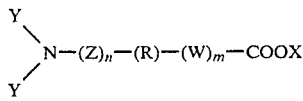

wherein Y is H or lower alkyl; Z is CH$_2$; n is 0 or 1; R is alkylene or cycloalkylene; X is H, acyl or lower alkyl; m is 0 or 1; W is CH$_2$; and the non-toxic pharmaceutically acceptable salts thereof.

The allergic material which may be employed in the practice of this invention may be those materials which contain allergens to which patients are sensitive and to which these sensitive patients have allergic reactions. Included in the allergic materials which may be employed in the practice of this invention include such allergen containing materials as pollens, fungi, molds, animal danders or epithelial products, various dust components, including house dust components, insects, for example, house mites, ticks or fleas, foods, infectious agents, contactants and other various recognized allergen containing products and substances. Most satisfactory results have been obtained in the practice of this invention when the allergic material employed is selected from the group consisting of mites, molds and mold spores, tree, grass and weed pollens, and combinations of the foregoing, although other allergic materials may also be successfully employed.

The suitable extraction solvent which may be employed in the practice of the instant invention may be any solvent which will satisfactorily extract the allergens from the allergic material, and/or which will be suitable for systemic administration to the patient being treated, or alternatively is capable of being completely removed from the extracted allergen-containing composition prior to its administration to the patient. Most preferably, it has been found that an aqueous solvent provides the most satisfactory result in the practice of this invention. However, the instant invention may be practiced by employment of any suitable solvent which can be used for the purposes required, including alcohols, such as ethanol; pyridine/aqueous alkaline extraction solutions; and other like solvents which are known to the skilled worker to be useful for such purposes.

The satisfactory practice of the instant invention requires that a small but effective amount of a compound of the formula,

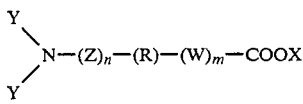

wherein Y, n, Z, R, m, W, and X are as hereinabove defined be incorporated in the solvent of extraction. By a small but effective amount it is hereby meant that the final concentration of the compound in the extraction composition should be between about 0.001 M and 0.5 M, and preferably between 0.025 M and 0.4 M, and most preferably between 0.05 and 0.2 M, although the other concentrations may also provide satisfactory results.

The compounds which are incorporated in the extraction solvent of the instant invention are those of the formula,

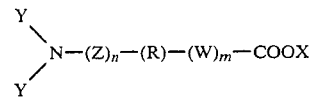

wherein Y, Z, n, R, W, m, and X are as hereinbefore defined. In the preferable embodiment of the instant invention, each Y may be H or lower alkyl; Z is CH$_2$; n is 0 or 1; W is CH$_2$; R is an alkylene group of the formula C$_r$H$_{2r}$, wherein r is an integer of from 4 to 8; X is H, acyl or lower alkyl; and the non-toxic pharmaceutically acceptable salts thereof. More preferably, in the practice of this invention, it has been found that optimum results are obtained when the compound employed is either or 6-amino-hexanoic acid, or trans-4(aminomethyl) cyclohexanecarboxylic acid, commonly known as epsilon-aminocaproic acid or tranexamic acid, respectively, although the other compounds of the above formula also provide satisfactory results.

The acyl moieties which may be employed in the practice of the instant invention include those acyl groups derived from hydrocarbon carboxylic acids of twelve carbon atoms or less, such as alkanoic acids, cycloalkanoic acids, monocyclic aryl carboxylic acids and the like.

The conditions under which the extraction of the allergic materials may be conducted are those under which such extraction procedures are usually performed, as is well known to the skilled worker. Thus, the extraction procedures may be performed at any temperature or under such atmospheric conditions as may provide the most optimum results as is appreciated by the skilled worker. The allergen containing extract composition obtained by the extraction of the allergic material with the solvent composition of this invention may then be treated in the same manner as any allergen containing extract. Thus, the allergen containing extract may be employed directly for diagnosis of therapeutic treatment of patients having an allergic condition, particularly in the case of diagnostic purposes any local reaction which is not of diagnostic importance will be inhibited; or alternatively, the said allergen containing extract may be further treated to obtain a composition having a higher, although innocuous, concentration of allergens; or as a further alternative the allergen containing extract may be taken down to dryness by any suitable procedure known to the skilled worker to accomplish this result without injury to the allergens, for example, lyophilization, for storage and reconstitution at a later date just prior to administration to the patient.

The allergen containing extract compositions obtained in the practice of this invention are more storageably stable over a longer period of time. In addition, upon systemic, for example, parenteral, administration to the patient, the compositions of this invention involve for commonly administered dose regiments, fewer and substantially less severe adverse reactions of the patient and are safer compositions than those of the prior art.

The instant invention may be further illustrated by the following examples:

EXAMPLE 1

An extraction solution comprised of pyrogen-free distilled water containing 0.1 M of epsilon-amino caproic acid, and having a pH of 7.0 was prepared. The resultant extraction solution was then employed to extract the allergens of Lolium perenne pollen, which was carried out under normal laboratory conditions of temperature and pressure to yield an allergen-containing extract solution having incorporated therein approximately 0.1 M of epsilon-amino caproic acid. To this final allergen containing solution was added a small amount of phenol as a preservative.

The foregoing procedure may be followed except that 0.001 M and 0.5 M of epsilon-amino caproic acid is substituted for the 0.1 M employed, with like results being obtained.

The foregoing procedure may be followed except that equivalent amounts of house dust components, mites, molds, ragweed pollen and animal danders may be employed in place of the Lolium perenne pollen to obtain like results.

EXAMPLE 2

In vitro tests to determine the specificity and potency of the allergen-containing extracts of the instant invention were conducted as follows:

An amount of grass pollen (Lolium perenne) was extracted with extraction solutions of the following compositions:

1. Pyrogen-free distilled water containing 0.1 M sodium bicarbonates pH=7.0.
2. Pyrogen-free distilled water containing 0.154 M sodium phosphate, pH=7.0.
3. Pyrogen-free distilled water containing 0.1 M epsilon aminoproic acid (EACA), pH=7.0.

The resultant extracts were then tested on cellulose discs prepared and assayed according to the RAST method (RAST assay method commercially available from AB Pharmacia, Sweden) according to the following general procedure: Fifty micro-liters of inhibiting extract was incubated with 50 microliter of a highly positive grass pollen serum pool. After 3 hours of incubation, Lolium perenne allergen-coupled discs were added to the tubes. After 6 hours of incubation, discs were washed 3 times and incubated with 50 microliter of radiolabelled anti IgE for at least 6 hours. After washing, radioactivity was measured in a gammacounter and the % of inhibition was calculated.

RAST values for 6 individual sera were determined with discs coupled to Lolium perenne extract produced with Extraction solutions 1, 2 and 3, with discs obtained from AB Pharmacia serving as a control. Results are shown in FIG. 1.

Figure 2:
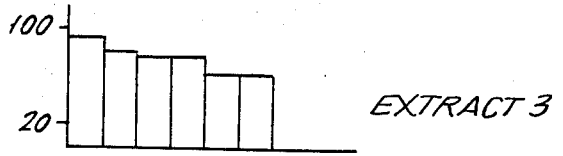
Figure 2:
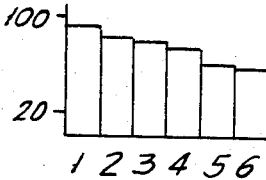

RAST values were determined for various dilutions of a positive serum pool with discs coupled to Lolium perenne extract produced with Extraction solution 1 and 3. Results are shown in FIG. 2.

Figure 3:
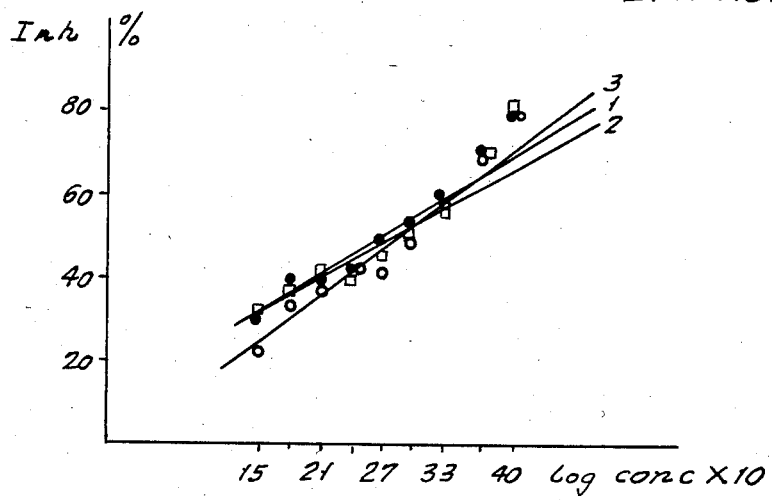

Extracts made with Extraction solutions 1, 2 and 3 were assayed by the RAST inhibition method. Results are shown in FIG. 3.

The results of these tests demonstrate that the compositions of the instant invention have the same potency as the prior art compositions.

EXAMPLE 3

The procedures of Example 1 may be followed except that an equivalent amount of tranexamic acid is substituted for the epsilon-amino caproic acid with like results being obtained.

EXAMPLE 4

In vivo tests were performed employing the allergen compositions of this invention. Lolium perenne allergen extract and house dust mite allergen extracts were prepared. The final extract had the following compositions:

A. Grass pollen allergens in pyrogen free distilled water containing 0.1 M-epsilon-aminocaproic acid.

B. Grass pollen allergens in pyrogen-free distilled water containing 0.15 M sodium phosphate.

C. House dust mite allergens in pyrogen-free distilled water containing 0.1 M epsilon-aminocaproic acid.

D. House dust mite allergens in pyrogen-free distilled water containing 0.15 M sodium phosphate.

Figure 4:
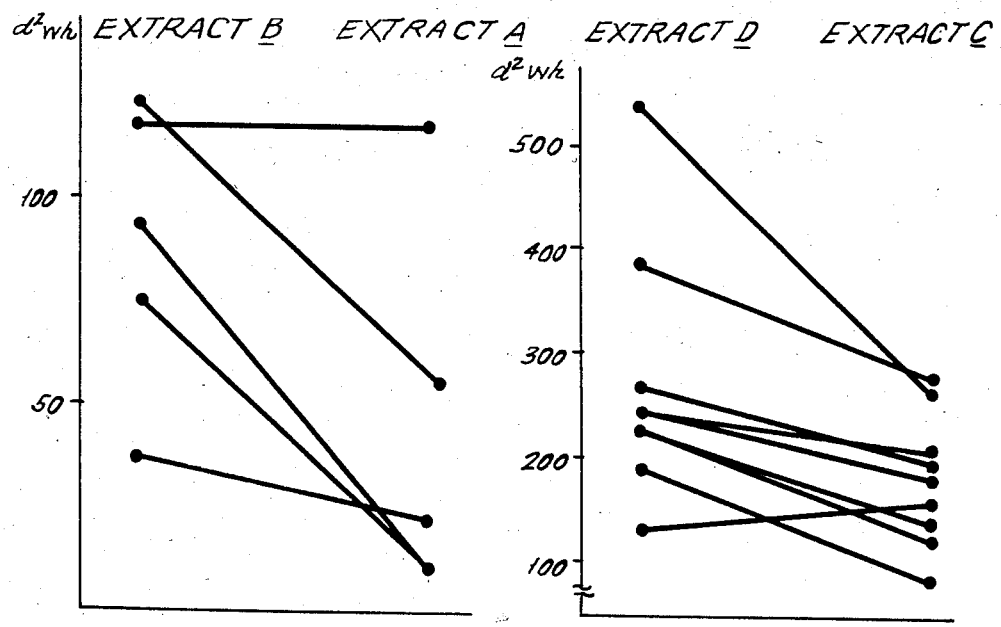

The respective final extracts (0.05 ml) were intradermally injected into the test subjects forearms at various sites at premeasured distances from each other. These skin tests were read fifteen minutes after administration. The wheal and flare reactions were delineated on a transparent sheet and the mean square wheal diameters ($d^2wh$) were calculated. The results are set forth in FIG. 4 and show that there is a significant decrease in the local reactions involved in the administration of the compositions of this invention.

EXAMPLE 5

The procedure of Example 4 may be followed except that equivalent amounts of tranexamic acid may be substituted for the epsilon-aminocaproic acid with like results being obtained.

The invention may be variously otherwise embodied within the scope of the appended claims.

What is claimed is:

1. In a method of producing a systemically administerable allergen containing extract which is suitable for use in the diagnosis or therapeutic treatment of allergic conditions in patients which comprises extracting the allergic material with a suitable solvent and obtaining the allergen containing extract thus produced wherein the improvement comprises adding to the allergic material and solvent mixture a compound of the formula,

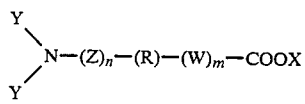

wherein Y is H or lower alkyl; Z is $CH_2$; n is 0 or 1; R is alkylene or cycloalkylene; X is H, acyl or lower alkyl; m is 0 or 1; W is $CH_2$; and the non-toxic, pharmaceutically acceptable salts thereof, and wherein the compound is present in a concentration of from 0.001 M to 0.5 M.

2. The method of claim 1 wherein the compound is 6-aminohexanoic acid.

3. The method of claim 1 wherein the compound is trans-4(aminomethyl) cyclohexane carboxylic acid.

4. In a composition suitable for use in the diagnosis or therapeutic treatment of an allergic condition in patients which comprises an allergic substance incorporated in a liquid non-toxic pharmaceutically acceptable systemically administerable vehicle wherein the improvement comprises the addition of a compound of the formula:

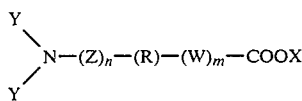

wherein Y is H or lower alkyl; Z is CH$_2$; n is 0 or 1; R is alkylene or cycloalkyene; X is H, acyl or lower alkyl; m is 0 or 1; W is CH$_2$; and the non-toxic pharmaceutically acceptable salts thereof, and wherein the compound is present in a concentration of from 0.001 M to 0.5 M.

5. The composition of claim 4 wherein the compound is 6-amino hexanoic acid.

6. The composition of claim 4 wherein the compound is trans-4(aminomethyl) cyclohexane carboxylic acid.

7. In a method of producing a systemically administerable allergen containing extract which is suitable for use in the diagnosis or therapeutic treatment of allergic conditions in patients, which comprises extracting the allergic material with a suitable solvent and obtaining the allergen containing extract thus produced wherein the improvement comprises adding to the allergic material and solvent mixture a compound of the formula,

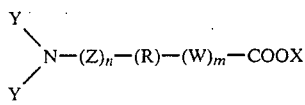

wherein Y is H or lower alkyl; Z is CH$_2$; n is 0 or 1; m is 0 or 1; W is CH$_2$; R is an alkylene group of the formula C$_r$H$_{2r}$, wherein r is an integer of from 4 to 8; X is H, acyl or lower alkyl; and the non-toxic pharmaceutically acceptable salts thereof, and wherein the compound is present in a concentration of from 0.001 M to 0.5 M.

8. In a composition suitable for use in the diagnosis or therapeutic treatment of an allergic condition in patients which comprises an allergenic substance incorporated in a liquid, non-toxic, pharmaceutically acceptable, systemically administerable vehicle wherein the improvement comprises the addition of a compound of the formula,

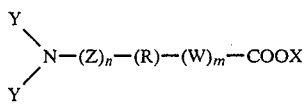

wherein Y is H or lower alkyl; Z is CH$_2$; n is 0 or 1; m is 0 or 1; w is CH$_2$; R is an alkylene group of the formula C$_r$H$_{2r}$, wherein r is an integer of from 4 to 8; X is H, acyl or lower alkyl; and the non-toxic, pharmaceutically acceptable salts thereof, and wherein the compound is present in a concentration of from 0.001 M to 0.5 M.

* * * * *